US006086538A

United States Patent [19]
Jørgensen et al.

[11] Patent Number: 6,086,538
[45] Date of Patent: Jul. 11, 2000

[54] METHODS AND APPARATUS FOR EVALUATION OF BONE CONDITION

[75] Inventors: Lars V. Jørgensen; Christian C. Bürger, both of Copenhagen, Denmark

[73] Assignee: Osteometer Meditech A/S, Horsholm, Denmark

[21] Appl. No.: 09/081,936

[22] Filed: May 21, 1998

Related U.S. Application Data

[63] Continuation of application No. PCT/EP96/05030, Nov. 15, 1996.

[30] Foreign Application Priority Data

Nov. 22, 1995 [GB] United Kingdom .................... 9523842
May 7, 1996 [GB] United Kingdom .................... 9609448

[51] Int. Cl.$^7$ ...................................................... A61B 8/00
[52] U.S. Cl. .......................................................... 600/449
[58] Field of Search ................................. 600/437–439, 600/442, 443, 449; 73/597, 599

[56] References Cited

U.S. PATENT DOCUMENTS

| | | |
|---|---|---|
| 4,774,959 | 10/1988 | Palmer et al. . |
| 4,913,157 | 4/1990 | Pratt et al. . |
| 5,042,489 | 8/1991 | Wiener et al. . |
| 5,119,820 | 6/1992 | Rossman et al. . |
| 5,218,963 | 6/1993 | Mazess . |
| 5,353,797 | 10/1994 | Matsushima et al. .................... 600/447 |
| 5,603,325 | 2/1997 | Mazess et al. ............................ 600/442 |
| 5,840,029 | 11/1998 | Mazess et al. ............................ 600/442 |

FOREIGN PATENT DOCUMENTS

| | | |
|---|---|---|
| 93/25146 | 12/1993 | WIPO . |
| 95/26160 | 10/1995 | WIPO . |

OTHER PUBLICATIONS

Laugier et al., "Broadband Ultrasonic Attenuation Imaging: A New Imaging Technique of the OS Calcis", Calaified Tissue, Feb. 1994, New York (US) pp. 83–86, XP000614385.
Fournier et al., "Clinical Assessment of Observer Independent Measurement of BUA and Ultrasound Velocity Using BUA Imaging of the OS Calcis", 10th Conference of the European Society of Biomechanics, Aug. 28–31, 1996.
Fournier et al., "Clinical Assessment of Ultrasound Parametric Imaging in Osteoporosis", 21st International Symposium on Ultrasonic Imaging and Tissue Characterization.
Fournier et al., "BUA Imaging (BAUI): Clinical Assessment of an Automatic ROI of Minimum Mean BUA Valve", World Congress on Osteroporosis 1996.
"UBIS 3000—The Ultrasound Bone Imaging System", Commerical Leaflet.
Calcified Tissue, vol. 54, No. 2, Feb. 1994, New York (US) pp. 83–86, XP000614385, P.Laugier et al "Broadband Ultrasound Attenuation Imaging: A New Imaging Technique of the OS Calcis".

*Primary Examiner*—Francis J. Jaworski
*Attorney, Agent, or Firm*—Pillsbury Madison & Sutro LLP

[57] ABSTRACT

A method of evaluating the status of bone tissue useful in the diagnosis of osteoporosis measuring a characteristic of ultrasound transmission through the calcaneus at a number of locations at an image forming degree of spatial resolution, deriving from said measurements information regarding the location of an approximately circular (as seen by measurements from the side) area of reduces attenuation in the calcaneus, optionally making further ultrasound measurements which reflect said bone tissue status, and evaluating said bone tissue status based on such said measurements and/or said further measurements at said location.

6 Claims, 3 Drawing Sheets

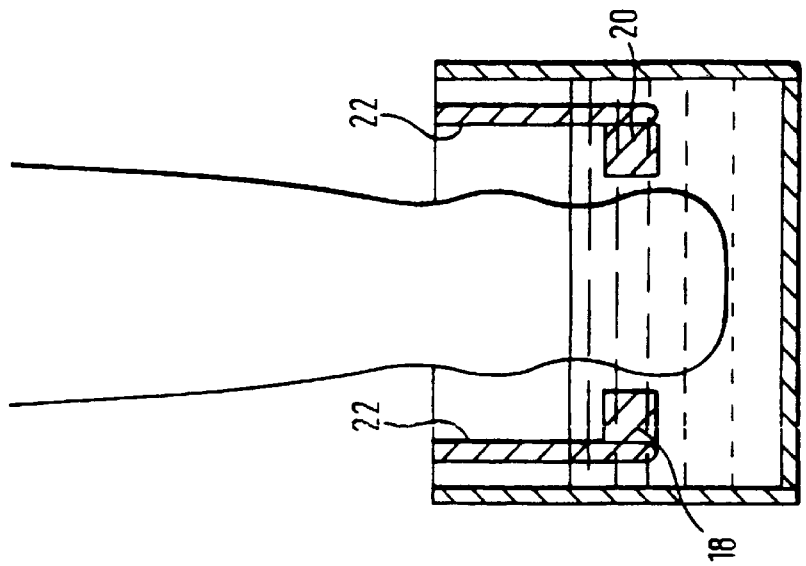
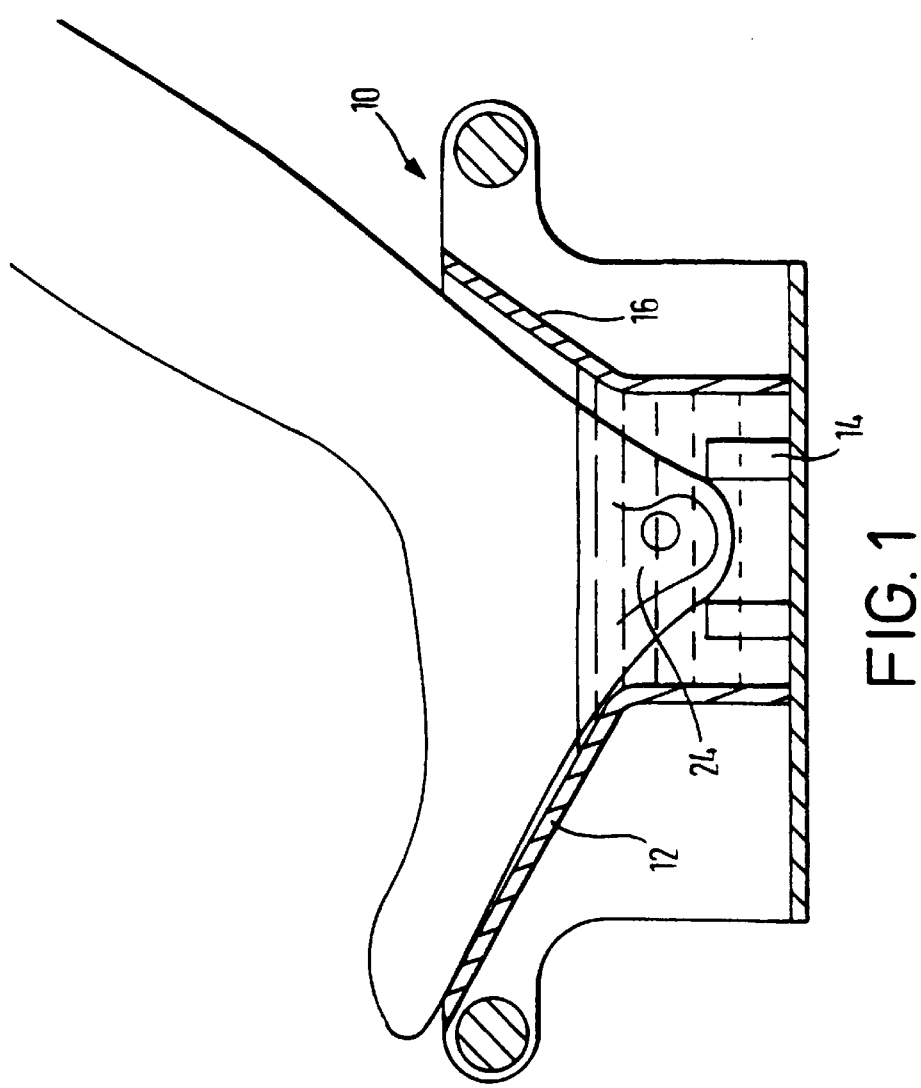

METHODS AND APPARATUS FOR EVALUATION OF BONE CONDITION

This is a Continuation of International Appln. No. PCT/EP96/05030 filed Nov. 15, 1996 which designated the U.S.

The present invention relates to methods and apparatus for use in the evaluation of the condition of bone. Such measurements are of value in diagnosing bone diseases and other abnormal bone conditions including principally osteoporosis.

Bones are composed of cortex (compact bone) and trabeculae (connective strands). Regions of bone that experience relatively high stresses tend more toward cortical bone. Regions of bones experience low stress tend to be more trabecular. In most sites of trabecular bone, the trabecular mass is surrounded by a relatively thin layer of cortical bone which may vary in thickness between individuals.

Osteoporosis is a disease of unknown cause which afflicts people, generally as they age. Osteoporosis affects women more often than men. It is manifest as absolute decrease in bone tissue mass. The bone that remains is, however, normal. A person suffering from osteoporosis loses a greater proportional amount of trabecular bone than cortical bone.

There is a need to be able to take a measurement on a patient and to relate the result reliably to the results of similar tests on a large number of men and women of different ages so as to gain information on whether the patient is at increased risk of fracture. It is also beneficial to generate an historical record of the changes in some property of the individual patient's bones and to make a diagnosis on the basis of historical trends.

These requirements imply a need to be able to repeat the measurement reliably on the same patient at different times and to make the measurements on many different patients in a consistent way.

A number of methods of ultrasound determination of bone condition have been proposed. U.S. Pat. No. 4,774,959 (Palmer) describes an apparatus in which a bone containing body member to be tested is placed between a pair of transducers and a pre-determined sequence of tone signals having frequencies spanning a range from 200 to 600 kHz is transmitted through the body member. Amplitudes of the received signals are stored and compensated using equivalent values obtained in the absence of the body member. From the measured amplitudes, there is calculated the rate of change of attenuation of ultrasound transmission of the body member with respect to frequency. Such measurements have come to be referred to in this art as broadband ultrasound attenuation or BUA measurements. There is also described the measurement of the speed of ultrasound transmission in the body member (SOS) Measurements are in practice conducted on the heel bone of the patient and the apparatus used includes a jig or clamp to ensure that the patient's heel bone is located between the transducers.

U.S. Pat. No. 4,913,157 (Pratt) describes similar apparatus but transmits a range of ultrasound frequencies simultaneously and derives a received ultrasound spectrum which is processed mathematically by methods including Fourier transformation to derive a signal indicative of bone condition. Speed of sound measurements are also made. It is indicated that various bone sites may be used for test purposes but the knee-cap is preferred.

U.S. Pat. No. 5,119,820 (Rossman) discloses apparatus for use in ultrasound bone density measurements in which the necessary pair of ultrasound transducers are mounted on the arms of a caliper so that they may be placed either side of the bone under test. Rossman notes that using prior art densitometers it was often necessary to position the instrument precisely relative to the body member of the patient being measured to have useful results because of heterogenities in the bone mass and structure of actual body members. He notes that a measurement taken at one location of density may be significantly different from a measurement taken close by and that prior art instruments therefore fixed the body member precisely so that measurement could be taken at the precise location each time. Instead of such a procedure he uses larger transducers to reliably cover at least one common region of interest in each measurement.

Alternatively, he also describes the use of an array of ten smaller transducers, with selection of the most appropriate one from which to derive information being carried out to try to make reproducible the specific measurement location. However, with an array of only ten transducers, this will not really be practicable.

Laugier et al in "Broad Band Ultrasonic Attenuation Imaging: A new imaging technique of the os calcis"—Calcif. Tissue Int. (1994) 54:83–86 describes scanning the os calcis in the X and Y directions at 1 mm intervals until pliers holding the sample bone in the ultrasound field are seen. An image of 70×70 pixels derived from the measured BUA at each scanning location is produced and a 1 cm square region of interest (ROI) is selected in the middle of the posterior part of the os calcis. Average values of BUA over 100 readings for the ROI are calculated. It is commented with reference to previous procedures that the predominant factor of error is due to the difficulty of defining a specific zone for the measurement and then finding it again for further measurements and that the averaging of the BUA over the ROI yields a low intrasystem error. The placement of the ROI is said not to be dependent on the spatial resolution of the imaging as it is always possible to relocate the ROI according to predefined criteria such as distances from the edges of the bone or by image superposition.

The methods described above for overcoming the difficulty of repeatably measuring the same location of a patient's bone are not satisfactory. It is necessary not only to ensure that measurements made on the same patient at different times are comparable because they have been made at the same location on the selected bone but also that the nature of the bone measured is constant between different patients whose bones may be of different size and positioned differently within the fleshy parts of the relevant body member. Furthermore, defining the area at which measurements will be taken with reference to the exterior of the bone fails to take adequate account of the fact that the thickness of the cortical layer of bone may vary between patients and within a single bone.

The present invention now provides a method of evaluating the status of bone tissue in vivo comprising measuring a characteristic of ultrasound transmission through a selected bone at a number of locations at an image forming degree of spatial resolution, deriving from said measurements information regarding the location of a selected internal anatomical feature of the selected bone, optionally making further ultrasound measurements which reflect said bone tissue status, and evaluating said bone tissue status based on such said measurements and/or said further measurements made at a location spatially defined with reference to said internal anatomical feature of the selected bone as detected by said ultrasound measurements.

The characteristic of ultrasound transmission measured is preferably attenuation but may be speed of sound (SOS) or broad band ultrasound attenuation (BUA).

Whilst the invention may be applied to various bones, it is preferable that the bone is one having a high trabecular content and most preferably the bone is the calcaneus (also known as the calcaneum or the os calcis).

We have discovered that when sufficiently precise measurements are made from side to side through of the calcaneus, an approximately circular area of reduced attenuation is found adjacent the lower end of the calcaneus.

The circular configuration is typical of the appearance of this area as seen by measurements of ultrasound attenuation or speed of sound from the side of the calcaneus, i.e. with transducers positioned either side of the patient's heel. It appears to relate to an area within the trabecular part of the bone where the network structure of the trabecular bone is more open and less dense. This anatomical feature is found to be highly reproducible between patients and provides an excellent reference point from which to locate the desired site of measurement in evaluating the status of bone tissue.

Preferably, the said further measurements upon which the evaluation of the bone tissue status is based are taken within said circular area. Preferably, the measurements are made at the centre of the circular area or within 5 mm from the centre. References herein to measurements being taken at a particular location should be understood as indicating that the centre of the transducer is located over the said location.

Preferably, measurements for use in the method of the invention are made over an area at a spacing between measurement locations of no more than 5 mm, suitably by scanning a pair of transducers over the area taking measurements periodically.

Preferably, the measurements are made a spacing of no more than 2 mm, more preferably at a spacing of from 0.1 to 1 mm, e.g. 0.5 mm.

The area scanned is preferably of at least 200 sq mm, more preferably at least 1,000 sq. mm, e.g. about 3000 to 5000 sq. mm.

Apart from the measurements needed to locate the anatomical feature from which the location at which to derive information regarding the bone condition is defined, further measurements may be needed to form the basis of the evaluation of bone condition. Where attenuation measurements are used to locate the anatomical features the further measurements preferably include measurements of the speed of sound transmission in the bone (SOS) and measurements of the broadband ultrasonic attenuation (BUA). Of course, if the location finding measurements are of SOS or BUA, no further measurements are necessarily needed both the location finding measurements and the or any further measurements are preferably all made at the same time as the transducers are scanned. Methods are known in the art for measuring these parameters and generally the methods described by Palmer in U.S. Pat. No. 4,774,959 may be used. One may provide a measurement relating to bone integrity based on the product of said BUA measurement and the transit time or SOS through said bone, e.g. of the kind described in U.S. Pat. No. 5,042,489. Alternatively or additionally, one may provide based on said BUA and/or SOS measurements an estimate of bone mineral density, e.g. as described in U.S. Pat. No. 5,218,963.

Thus, the BUA measurement may be made by sending an ultrasound signal from a first transducer positioned at one side of a bone such as the heel of a patient to a second transducer positioned at the opposite side of said bone sequentially at each of a number of selected frequencies at each measurement location and measuring the amplitude of the signals received at said second transducer relative to the amplitude of the transmitted signals and deriving from said relative amplitudes the first derivative of the attenuation with respect to frequency.

Preferably, the attenuation measurements at each frequency and the speed of sound measurements are made over the whole of the area within which the anatomical feature in question is located and in which the evaluation measurements are required. From the collected data, the position of the anatomical feature is deduced by consideration of say the attenuation measurements, the desired position of measurement for evaluation purposes is determined and the SOS and BUA values for that location are then deduced from the body of data.

Preferably, an image is derived from the attenuation measurements and is displayed to the person conducting the investigation.

The invention includes apparatus for evaluating the status of bone tissue comprising a first transducer for positioning on one side of a bone to be evaluated, a second transducer for positioning on an opposite side of said bone, means for transmitting ultrasound signals from one said transducer and for receiving said signals at said other transducer at each of a number of selected frequencies, means for scanning said transducers over an area of the said bone, means for measuring from said transmitted and received signals a characteristic of ultrasound transmission (e.g. attenuation) at different locations within said area, such as to define the location of a selected internal anatomical feature of said bone, and means for measuring from said transmitted and received signals the variation of ultrasound attenuation with frequency and/or the speed of ultrasound transmission at a location defined with reference to said anatomical feature.

The apparatus preferably includes means for producing and displaying an image based on said attenuation measurements. Optionally, means may also be provided for producing and displaying an image based upon said variation of BUA measurements over the area scanned and/or an image based on measurements of the speed of ultra-sound transmission over the area scanned. However, these latter parameters need only be calculated for a specific location defined with reference to the anatomical feature in question.

Preferably, means is provided to allow an operator to select a location or locations within said image of attenuation at which said variation and/or speed of sound transmission will be measured.

The frequency at which the attenuation measurements used to deduce the position of the anatomical feature of interest are made may preferably be selected within the range 200 kHz to 1 MHz, more preferably within the range of 400 to 600 kHz, i.e. around 500 kHz.

The invention includes a method of evaluating the status of the bone tissue of the calcaneus comprising carrying out measurement of at least one parameter indicative of the status of bone tissue at that part of the calcaneus characterized by being a limited internal zone of trabecullar bone of reduced density located towards the lower end of the calcaneus. The measurement of the parameters need not be ultrasonic but may be by other methods including X-ray or NMR scanning e.g. computer aided tomography, X-ray densitometry, neutron activation analysis, or single or dual photon absorptiometry.

The zone in which to carry out measurements may be located by ultrasound attenuation scanning as described above or by other methods e.g. by X-ray densitometry.

The invention will be further described and illustrated with reference to the following description of a preferred embodiment with reference to the accompanying drawings in which:

FIG. 1 is a side view of a measurement chamber of apparatus according to the invention;

FIG. 2 is an end view of the apparatus of FIG. 1;

Figure 3:
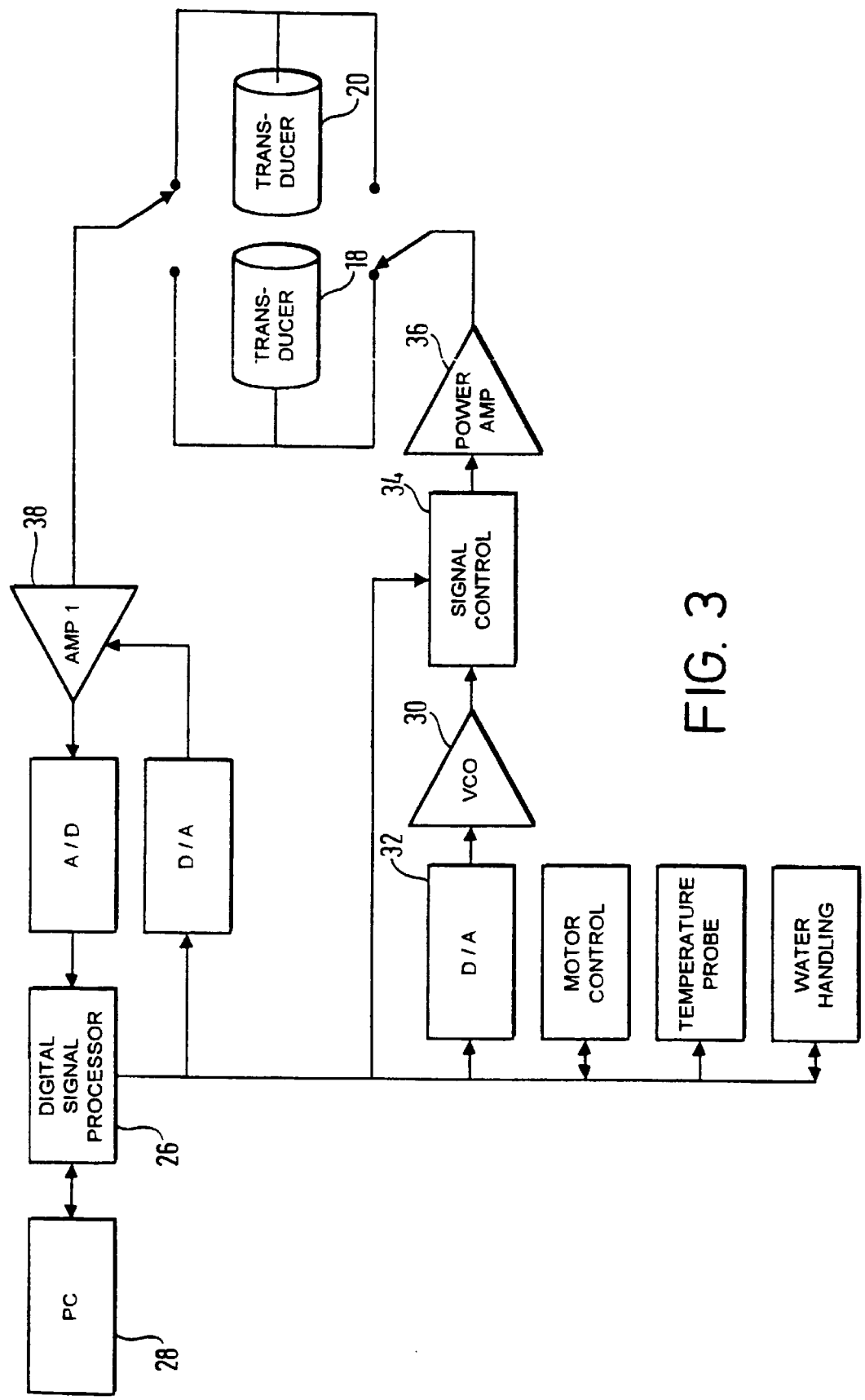
FIG. 3 is a block diagram illustrating the circuitry used in connection with the chamber of FIG. 1

As shown in FIG. 1 and FIG. 2, apparatus for use in the invention may preferably comprise a measurement chamber 10 for receiving the heel of a patient. The chamber contains a reference liquid which is preferably water in which the patient's heel is immersed. A rest 12 is provided for the sole of the patient's foot, a rest cup 14 is provided to receive the base of the patient's heel and back rest 16 is provided to support the lower part of the patient's calf so as approximately to position the patient's calcaneus in a suitable position for scanning. However, it will be noted that the precise location of the patient's foot is not relied upon. As seen in FIG. 2, the apparatus comprises a first ultrasound transducer 18 and a second ultrasound transducer 20 positioned either side of the position of the patient's heel and supported on arms 22. The arms 22 are connected by mechanical linkages (not shown) to drive motors enabling them to be scanned in synchrony along an X and a Y axis over a rectangular area corresponding generally in size to the part of the calcaneus 24 visible in FIG. 1.

As shown in FIG. 3, each of the two transducers 18, 20 is connected to operate either as a transmitter or as a receiver. The system illustrated in FIG. 3 may be divided notionally into five blocks namely a transmitter block, a receiver block, a motor movement control block, a temperature measurement block and a water handling block. All five blocks are controlled by a number of digital signal processors (DSP's) with one of these, the "master", being in overall control and the rest assigned to data-handling. The master DSP 26 communicates with a computer 28 used for data-handling and presentation and the control of the area scanned.

The transmitter block includes a Voltage Controlled sine-Oscillator (VCO) 30 supplied through a digital analog converter 32 and controlled by a signal control unit 34 to produce frequencies between 100 kHz and 1 MHz which are fed via a power amplifier 36 to the transducers 18, 20. The receiver circuit connected to the transducers 18, 20 includes an amplifier 38 for amplifying the received signal which is sampled and read into a DSP which examines the signal and adjusts the gain if the amplitude of the signal is outside predetermined limits.

The motor control block is used for positioning the transducers in the horizontal and vertical directions so that a selected area can be measured by moving the transducers in a scanning pattern.

The temperature of the water or other reference liquid around the foot is registered using a temperature sensor. The last block represents water handling facilities including cleaning, heating and level control means.

In use, a scan is performed by moving the transducers 18, synchronously in the horizontal and vertical directions to scan over an area. As the transducers move, signals are emitted from one transducer and are received by the other in transmission mode and received by the transmitting transducer in pulse echo mode or reflection mode.

Reflected signals are used to estimate the distance from each transducer to the skin at each location in the scan using the formula:

$$d = \frac{tv_{water}}{2}$$

where d is the distance from a respective transducer to the foot, t is the time from emitting to receiving the reflected signal, and $v_{water}$ is the speed of sound in water. When the distance from the transducer to the skin is known for each side, the speed of sound (SOS) in the foot can be derived from the formulae:

$$L = d_1 + d_2 + t_f v_f \text{ and } T = \frac{t1}{2} + \frac{t_2}{2} + t_f$$

where L is the distance between the transducer, $d_1$ and $d_2$ are the distances to the transducers on each side of the foot, $t_f$ is the transit time in the foot, $v_f$ is the speed of sound in the foot (SOS-value), T is the time from emitting a signal on one side of the foot until receiving it on the other side and $T_1$ and $T_2$ are the time from emitting to receiving the reflected echo on each respective side of the foot.

Figure 4:
FIG. 4 is an image produced by processing of attenuation data derived from the apparatus illustrated in FIGS. 1 to 3.

The amplitude of the received signal is logged and displayed by the computer in the form of an image of the calcaneus based on the amplitude of the received signal as a measure of attenuation as shown in FIG. 4. As is clearly seen in FIG. 4, there is a darker area of approximately circular shape at the position indicated in the X and Y directions by the side bars at the head of a teardrop shaped area. This has been found to be a constant feature seen in attenuation scans of this kind on different patients by which a significant and repeatable position within the calcaneus of different patients and the same patient on different occasions may be located and defined.

During the scan described above, attenuation is preferably measured at each location at a desired number of frequencies, preferably at least four frequencies, e.g. about eight frequencies. Suitably, the frequencies are in the frequency range of 1 kHz to 1 MHz, more preferably within the range 200 to 600 kHz. Preferably the frequencies are substantially evenly spaced within the frequency range. The BUA may be calculated at each scanned location as the slope of the attenuation as a function of the ultrasonic frequency. The attenuation K may be calculated according to the formula:

$$K = 20 \text{ LOG} \left[ \frac{A_{water}}{A_{foot}} \right]$$

where $A_{foot}$ is the amplitude of the signal with the foot submerged in bath and $A_{water}$ is the amplitude of the signal through the water alone. The BUA is then calculated as the slope of the linear regression of a number of attenuations corresponding to different frequencies.

At each frequency and at each location, the amplitude signals may be measured many times and the received signals may be added before further calculation in order to suppress white noise influence.

Whilst moving the transducers, signals may be continuously emitted, received and calculated, so that the final result is an array where each entry describes a physical location in the foot. For each point, three values may be calculated and stored namely the SOS, BUA and an attenuation at a selected frequency. The PC 28 may then display the values as images on a screen.

Either automatically using image recognition procedures or by the intervention of an operator, the anatomical feature to be used may be identified in the attenuation image and SOS and/or BUA values relating to selected area may then be read out.

Because of the ability to locate the same specific area within the heel bone of different patients, normal and pathological ranges may be established for BUA and SOS values based upon measurements of a large number of healthy patients and patients with pathology of different ages. Clinically significant inferences may the be drawn from the readings of a given patient as compared with the normal range thus obtained for patient age and sex.

Whilst the invention has been described with reference to the specific embodiment, many variations and modifications may be made within the scope of the invention.

What is claimed is:

1. A method of evaluating the status of bone tissue comprising measuring a characteristic of ultrasound transmission through a selected bone at a number of locations using a movable ultrasound transducer which is scanned over a body part containing said bone tissue so as to make said measurements at locations within an area at a spacing between measurement locations of no more than 5 mm, deriving from said measurements information regarding the location of a selected internal anatomical feature of the selected bone, and evaluating said bone tissue status based on ultrasound measurements which reflect said bone tissue status made at a location spatially defined with reference to said internal anatomical feature of the selected bone.

2. A method as claimed in claim 1, wherein said selected bone is the calcaneus.

3. A method as claimed in claim 1, wherein said anatomical feature is an approximately circular, as seen by measurements from the side by measurements from the side of the selected bone, area of reduced attenuation or a selected part of said area.

4. A method as claimed in claim 3, wherein said bone tissue status evaluation is based on measurements made within said circular area.

5. A method claim 1, wherein said measurements are made at a spacing of no more than 2 mm.

6. A method as claimed in claim 1, wherein said measurements are made at a spacing of from 0.1 to 1 mm.

* * * * *